United States Patent [19]

Ohlrogge

[11] 4,230,485

[45] Oct. 28, 1980

[54] METHOD OF INCREASING GRAIN YIELD IN FIELD CORN BY APPLICATION OF TRIACONTANOL

[75] Inventor: Alvin J. Ohlrogge, West Lafayette, Ind.

[73] Assignee: Purdue Research Foundation, West Lafayette, Ind.

[21] Appl. No.: 960,762

[22] Filed: Nov. 14, 1978

[51] Int. Cl.$^3$ ............................................. A01N 31/02
[52] U.S. Cl. ..................................................... 71/122
[58] Field of Search ......................................... 71/122

[56] References Cited

U.S. PATENT DOCUMENTS 4,150,970  4/1979  Ries et al. ............................... 71/122

OTHER PUBLICATIONS

Ries et al., Science, vol. 195 (1977), pp. 1339–1341.
Wall Street Journal, Nov. 15, 1977.

*Primary Examiner*—Catherine L. Mills
*Attorney, Agent, or Firm*—John R. Nesbitt

[57] ABSTRACT

A field corn specific method of treatment with 1-triacontanol [$CH_3(CH_2)_{28}CH_2OH$] which produces a significant yield increase is disclosed. The method teaches that the stage of plant maturity is the key to the attainment of increased yields in field corn. Foliar applied rates from about 2 mg per acre to about 56 mg per acre are equally effective, which makes widespread commercial farm use practical.

7 Claims, No Drawings

METHOD OF INCREASING GRAIN YIELD IN FIELD CORN BY APPLICATION OF TRIACONTANOL

FIELD OF THE INVENTION

This invention relates to plant growth regulators, and more particularly to a field corn specific use of triacontanol as a corn yield enhancer.

BACKGROUND OF THE INVENTION

As early as 1975 it was reported by Dr. S. K. Ries and associates in the Michigan Agricultural Experiment Station Journal article No. 7431, that coarsely chopped alfalfa hay, when applied to the soil as a band adjacent row crops could improve plant growth. This phenomenon was mentioned with respect to lettuce, rice, cucumbers, tomatoes, cauliflower and field corn. The authors stated that "The cause of this response is not clear. The magnitude and characteristics of the response (Shoot/root ratios) to such small quantities of alfalfa indicate that the direct availability of nitrogen from alfalfa is not the likely cause." Ries and his co-workers speculated in this bulletin about the cause of the response but did not mention the possible presence of a growth stimulant, and in fact concluded the article by stating that "These results suggest that sidedressing crops with small quantities of plant material may increase the efficiency of fertilizer utilization or substitute for supplemental application of synthetic or inorganic nitrogen fertilizers."

Then, in an article that appeared in *SCIENCE, Mar. 25, 1977*, Volume 195, pp. 1339–1341, Ries and his co-workers reported the isolation of triacontanol as the active growth agent that had been present in the earlier alfalfa work, and the laboratory scale foliar application to field corn of a solution containing 0.01 mg per liter up to 1.00 mg per liter was reported also. The results for field corn showed only that the mg/shoot was 466 for the 0.01 rate and 429 at the 1.00 rate. The authors concluded that the "corn grew best when sprayed with 0.01 mg/liter, whereas rice grew best at the higher concentration."

Then, in 1977, Dr. Ries and others conducted field tests under the auspices of the Pesticide Research Center, Department of Horticulture, Michigan State University, at East Lansing, Michigan. The results of the trials were reported by a bulletin of the Research Center entitled "Yield of Crops Sprayed with Triacontanol in Field Plots During 1977" by Dr. Stanley Ries and Terry Richman.

The bulletin reports the following general results:

| | SUMMARY OF RANGE AND SIGNIFICANCE OF INCREASES DUE TO TRIACONTANOL ON MARKETABLE YIELD OF ALL CROPS SPRAYED IN THE FIELD DURING 1977. | | |
|---|---|---|---|
| | Range of increase over control | | Odds that increase was not due |
| Crops | (tons/ha) | (%) | to chance* |
| Dry Beans | .08 to .23 | 3 to 10 | 19:1 |
| Sweet Corn | 1.2 to 2.6 | 11 to 24 | 99:1 |
| Field Corn | 0 | 0 | N.S. |
| Cucumber | 1.3 to 2.3 | 6 to 19 | 99:1 |
| Tomatoes (Early yield) | .4 to 2.8 | 5 to 30 | 19:1 |
| Wheat | .04 to .20 | 0 to 8 | N.S. |
| Carrots | 3.0 to 5.8 | 11 to 21 | 19:1 |
| Radishes | 0 to .14 | 0 to 8 | 19:1 |
| Asparagus | .12 to .22 | 34 to 63 | 19:1 |
| Lettuce | 0 to 6.4 | 0 to 36 | N.S. |

*N.S. = not significant

The specific data respecting field corn was also reported as follows:

| YIELD OF FIELD CORN TREATED WITH FOLIAR APPLICATIONS OF TRIACONTANOL (AVERAGE OF 3 LOCATIONS). | |
|---|---|
| TRIACONTANOL (mg/l) | YIELD OF UNSHELLED CORN (metric tons/ha) |
| Control | 11.9 |
| .01 | 11.5 |
| .10 | 11.4 |
| 1.00 | 11.5 |

CONDITIONS:
Location—E. Lansing, Gratiot County and St. Joe County.
Fertilizer program—normal cultural practices.
Planting method—commercial corn planter.
Stage of crop—after corn had 3 to 6 leaves in all tests.
Plot size—15.2 M by 0.76 M.
Blocks—four to six.
Spray rate—388 l/ha with one 8004 nozzle.
Miscellaneous—Average of 3 locations and different number of applications of the different rates. There was no significant difference between number of applications or between rates.

Based on the previous Ries work and the 1977 field trials, it was reported in the Nov. 15, 1977 issue of the *Wall Street Journal* as follows:

"FAILURE WITH GRAIN CROPS"

In the tests at Michigan State, the chemical failed to increase the yields of wheat or field corn, which are the largest grain crops in the U.S.

However, Mr. Ries said, agronomists at Purdue University have reported that it did increase field-corn yields on test plots in Indiana this year. Mr. Ries suggested that the chemical's effect is affected by temperature and that it might have been too cold at the time it was tried in Michigan.

The Purdue University tests reported in the *Wall Street Journal* were supervised by Dr. A. J. Ohlrogge and have continued and now form the basis for this invention.

SUMMARY OF THE INVENTION

This invention provides a method of application of triacontanol to field corn which is suitable for use under commercial corn growing conditions.

It is, therefore, an object of this invention to provide a method for application of triacontanol to field corn growing in commercial size stands.

It is another object of this invention to provide specific parameters under which triacontanol can be applied to field corn to obtain maximum grain yield enhancement.

DESCRIPTION OF THE INVENTION

The following examples best exemplify and describe the present invention:

EXAMPLE 1

The triacontanol was applied on the foliage of corn at stages of development which were effective when 4,6,dinitro-o-sec butyl phenol, DNBP, was used to chemically stimulate corn yield. Five rates were used, namely: 0, 2, 6, 18, and 54 milligrams per acre of triacontanol. Two development stages for application were chosen, namely, from tassel initiation to one inch in length, and at a tassel length of 3 to 4 inches. In addition, a double application, i.e. an early plus late treatments were applied. These plots received 0, 4, 12, 36, and 108 milligrams of triacontanol per acre.

The hybrid chosen for this experiment, which was surrounded on three sides by replicated DNBP experiments, was Dennis 37. The corn was planted on May 12, 1977, using a six row planter. The planted population was in excess of 35,000 per acre and the corn was thinned in the seedling stage to a stand of 24,000 plants per acre. The individual plots were three rows wide—7.5 feet and 30 feet long. Experimental treatments were applied to all three rows. Twenty-six feet of the center row was harvested for yield and used for observing experimental effects.

The experimental design was a split block with five replications. Each of the five replicate blocks was divided into three sub-blocks, (early, late and early plus late). These sub-blocks were divided into the five rate plots. These rate plots were randomized within the sub-block.

The triacontanol was put into solution with chloroform as described by Ries, Science, Mar. 25, 1977, Vol. 195, pp. 1339–1341. The chloroform solution was added to water and Tween 20 was added at the rate of 0.5 pt. per 100 gallons of spray solution. The spray solution was applied as an overall broadcast spray at the rate of 50 gallons per acre, using a carbon dioxide pressured back pack sprayer and hand held boom with one nozzle per row. The early spray was applied on June 30 at 8:00 a.m. The weather was overcast with a temperature of 65° F. The late application was applied on July 10 at 7:45 a.m., the weather was hot, humid, hazy and the temperature was 75°.

Plot Preparation

The yield experiment with triacontanol applied to the foliage of corn was carried out at the Purdue University Agronomy Farm during the 1977 growing season. The prairie soil, Chalmers silty clay loam of field number 23 was in a high state of fertility. The residues of the previous crop of soybeans were plowed under in the fall. Six hundred pounds per acre of 0–28–21 was applied. The soil pH, 6.5, was ideal for corn. In the spring 260 pounds per acre of nitrogen as anhydrous ammonia was knifed in the soil. Normal soil preparation methods were used in preparing the seedbed.

An infestation of Canadian thistle in replicates three, four and five presented a problem. They were hoed out twice. The regrowth was still so great that these replications had to be discarded.

No visible treatment effects were observed in vegetative or reproductive growth of the plots. Standard harvesting procedures were used in determining the grain yields.

Differences in grain yields associated with rate of triacontanol when tested statistically were found to be insignificant and therefore could be ignored in testing the effect of time of application. Precision in this evaluation was thereby increased because eight replications were now available. The mean yield for the early application only was 149.9 bushels per acre, the late application only was 138.2 bushels per acre and the early plus late was 147.2 bushels per acre. The difference in yield between the late and the early or the late and the early plus late was significant at the six percent level of probability. One can conclude that the early triacontanol applications increased corn yields 10.3 bushels per acre or 7.5 percent. Only one untreated plot occurred in replicate one and two. It yielded 137.2 bushels per acre. This yield suggests about a ten bushel increase per acre when triacontanol was used as described.

EXAMPLE 2

The general experimental techniques used in 1978 were the same as those used in 1977 and described in Example 1. The experiment was carried out on field number 32 at the Purdue Agronomy Farm. The soil was again in a high state of fertility. Beck's 65X was the chosen test hybrid. The corn was planted May 26, and as in 1977, thinned to a stand of 24,000 plants per acre. The experimental treatments were applied on July 7 when the unemerged tassel was from 2 to $7\frac{1}{2}$ cms. long. Twenty (20) gal/acre of foliar sprays were applied beginning at 9:15 a.m. with temperature of 76°, an overcast sky with slight breeze and a small amount of dew on the corn. After spray application, no phytotoxic symptoms were observed. No. stimulation of vegetative growth was observed. The plots were observed closely and data was collected on tassel emergence, pollen shed, and maturity.

The growing conditions were near ideal except for excessive rain on June 25 which flooded parts of the experimental area for varying lengths of time, with water standing on the northeast extreme corner of the experiment for the longest period of time.

The corn was harvested the week of Oct. 1st using procedures that are previously described. The treatments and grain yields are outlined in Table I below.

TABLE I

| No. | TREATMENT* | Grain yield bu/acre | Increase over unt. | Difference | % |
|---|---|---|---|---|---|
| 1 | Untreated | 163.5 | | | |
| | | 160.4 | | | |
| 2 | Untreated | 157.3 | | | |
| 3 | Chloroform + Tween 20 | 159.3 | — | −1.1 | −0.6 |
| 4 | Triacontanol + Chloroform + Tween 20 | 164.6 | + | 4.2 | 2.6 |
| 5 | Triacontanol + Chloroform | 166.1 | + | 5.7 | 3.6 |
| 6 | Triacontanol + Acetone + Tween 20 | 170.2 | + | 9.8 | 6.1 |
| 7 | Triacontanol + Acetone | 170.7 | + | 10.3 | 6.4 |
| 8 | Triacontanol (Analab) + Chloroform | | | | |

TABLE I-continued

| No. TREATMENT* | Grain yield bu/acre | Increase over unt. | Difference | % |
|---|---|---|---|---|
| + Tween 20 | 162.8 | + | 2.4 | 1.5 |

*Triacontanol purchased from Shenandoah Chemical Company except for Treatment 8.
Spray solutions value: 20 gallons/acre
Triacontanol rate: 10 mg/acre
Tween 20: 0.05% by volume
Chloroform: 95 ml/acre
Acetone: 95 ml/acre The experimental design was that of a complete randomized block with five replications. The untreated plot was entered twice in each replication.

Examination of the data show that the presence or absence of the Tween 20 wetting agent had little or no effect on grain yields, (treatment 4 vs. 5 and treatment 6 vs. 7). Acceptance of this assumption results in being able to test the effect of triacontanol in two different solvents with ten replications. Analyses of variance of the sub experiments show that triacontanol formulations increased yields at a level of probability of 20 percent with the chloroform solvent, (treatment 4 and 5 vs. 1 and 2). The acetone formulation was superior to the chloroform (treatment 4 and 5 vs. 6 and 7) at a probability level of 7 percent and that the acetone formulation increased yields over the untreated with a probability level of 0.5 percent, (treatment 1 and 2 vs. 6 and 7).

The data also clearly indicate that the water-chloroform-Tween-20 mixture had no appreciable effect on grain yield, (treatment 3 vs. 1 and 2).

It can be concluded from the above two examples that:

1. Foliar applications of triacontanol increase corn yields in Dennis 37 and Beck 65 hybrids and probably all hybrid field corns.

2. That the rate of application does not appear to be critical in the range of 2 to 56 milligrams per acre.

3. The foliar application may best be applied from tassel initiation to 7 cm in length.

4. The dissolution of triacontanol in chloroform is an effective solvent procedure but acetone is a more effective solvent. Other solvents such as the amyl alcohols may be equally or more effective.

5. Applications were applied with ground equipment at spray volumes of twenty and fifty gallons per acre across the top. Other approved methods of aerial application and spray volumes according to the state of the art should be equally effective.

We claim:

1. The method of enhancing the grain yield of a field corn crop by applying triacontanol to the foliage of a corn plant at a rate of less than 112 mg per acre and at a growth stage of the corn plant after tassel initiation inside the corn plant.

2. The method in accordance with claim 1 in which said triacontanol is applied at a rate of between about 2 mg and about 56 mg per acre.

3. The method in accordance with claim 1 in which said triacontanol is applied in a solution which also contains chloroform.

4. The method according to claim 1 in which said triacontanol is applied in a solution which also contains acetone.

5. The method according to claim 3 in which said solution also contains a wetting agent.

6. The method according to claim 5 in which said triacontanol is applied in a solution which contains about 0.5 pint of wetting per 100 gallons.

7. The method according to claim 6 in which said solution is sprayed over said crop at a rate of between about 20 gallons and 50 gallons per acre.

* * * * *